(12) United States Patent
Groen et al.

(10) Patent No.: US 7,807,415 B2
(45) Date of Patent: Oct. 5, 2010

(54) METHODS OF PRODUCING STABLE B-LYMPHOCYTES

(75) Inventors: Herman Groen, Groningen (NL); Hans H. Westra, Zwaagwesteinde (NL)

(73) Assignee: IQ Therapeutics BV, Groningen (NL)

( * ) Notice: Subject to any disclaimer, the term of this patent is extended or adjusted under 35 U.S.C. 154(b) by 894 days.

(21) Appl. No.: 11/509,364

(22) Filed: Aug. 23, 2006

(65) Prior Publication Data

US 2007/0098711 A1    May 3, 2007

Related U.S. Application Data

(60) Provisional application No. 60/710,626, filed on Aug. 23, 2005.

(51) Int. Cl.
    *C12N 5/06*     (2006.01)
    *C12N 5/16*     (2006.01)
    *C12P 21/08*    (2006.01)
    *G01N 33/577*   (2006.01)

(52) U.S. Cl. .................. 435/70.21; 435/70.4; 435/326; 436/548

(58) Field of Classification Search ........................ None
    See application file for complete search history.

(56) References Cited

U.S. PATENT DOCUMENTS

| | | | |
|---|---|---|---|
| 5,641,638 A * | 6/1997 | Bredt et al. ................. | 435/7.32 |
| 5,776,778 A * | 7/1998 | Kajander et al. ............ | 435/405 |
| 6,297,052 B1 * | 10/2001 | Kehry et al. ................. | 435/377 |
| 2003/0153022 A1 | 8/2003 | Patti et al. .................. | 435/7.35 |
| 2003/0228322 A1 | 12/2003 | Schuman et al. ......... | 424/184.1 |
| 2007/0014720 A1 * | 1/2007 | Gazit-Bornstein et al. . | 424/1.11 |

FOREIGN PATENT DOCUMENTS

| | | | |
|---|---|---|---|
| EP | 0 322 762 | | 7/1989 |
| EP | 0347230 | * | 12/1989 |
| WO | WO 90/00404 | * | 1/1990 |
| WO | WO 93/19373 | | 9/1993 |

OTHER PUBLICATIONS

Galfre et al, Meth. Enzymol., 73, 3-45, 1981.*
Goding, Jour. Immunol. Meth., 39, 285-308, 1980.*
Harlow et al, Antibodies: A Laboratory Manual, Cold Spring Harbor Laboratory, 1988, pp. 196-225.*
Kanki et al., "Immortalization of plasma cells by plasmid DNA and its hybridoma", *Human Antibodies and Hybridomas*, 6(3):89-92 (1995).
Karpas et al., "A Human myeloma cell line suitable for the generation of human monoclonal antibodies", *PNAS*, 98(4):1799-1804 (2001).

* cited by examiner

*Primary Examiner*—David A Saunders
(74) *Attorney, Agent, or Firm*—Mintz, Levin, Cohen, Ferris, Glovsky and Popeo, P.C.; Cynthia A. Kozakiewicz; Ivor R. Elrifi

(57) ABSTRACT

The invention provides a method of producing a stable lymphocyte culture and methods of producing monoclonal antibodies.

15 Claims, 1 Drawing Sheet

METHODS OF PRODUCING STABLE B-LYMPHOCYTES

RELATED APPLICATIONS

This application claims priority to U.S. Ser. No. 60/710,626, filed Aug. 23, 2005 which is incorporated herein by reference in its entirety.

FIELD OF THE INVENTION

The invention relates to improving the survival and stability of cells after an immortalization procedure.

BACKGROUND OF THE INVENTION

The standard procedure for the generation of monoclonal antibodies as originally described by Köhler and Milstein in 1975 (Nature 256, 495-497) involves the fusion of sensitized murine spleen cells with murine myeloma cells in the presence of polyethyleneglycol (PEG). However, this method is rather inefficient. Usually, at best only one B-cell at $2 \times 10^5$ spleen cells successfully fuses. A great number of the cells are lost.

A major problem for the generation of human monoclonal antibodies is the fact that the hybridoma's generated are unstable in that they die, lose the ability to secrete antibody or stop proliferating shortly after the immortalization procedure.

Moreover, with traditional techniques only spleen cells can be used as the source of B-cells, because fusions with lymph node cells or peripheral blood cells only yield too limited a number of hybridomas or are not possible at all. Thus, a need exist for a method of producing human hybridomas that are stable.

SUMMARY OF THE INVENTION

The invention is based on the discovery that repeated oligoclonal handpicking unexpectedly improves one or more characteristics of antibody-producing cell (e.g., cells within an immortalized population). For example, oligohandpicking results in B-lymphocytes that are more stable (i.e., more likely to survive (e.g., survive and or proliferate for a longer period in culture)). Antibody producing cells that survive and or proliferate longer and more robustly produce more antibody as a result.

Accordingly, the invention features methods of producing a more stable B-lymphocyte or B-lymphocyte cell culture. Stable B-lymphocytes are produced by immortalizing the population of B-lymphocytes and separating plurality of cells from the population to yield a first oligoclonal cell culture. By plurality of cells is meant a clump of cells containing at least 5, 10, 20, 30, 40, 50 or more cells. Separating the plurality of cells is accomplished for example by oligoclonal handpicking. The B-lymphocytes are provide from a donor.

Optionally, it is determined whether the first oligoclonal cell culture has an improved characteristic, and maintaining the oligoclonal cell culture in a solution that promotes cell viability. The improvement may be relative to the population of B-lymphocytes from which the oligoclonal population was derived or to a population of antibody-producing cells produced by a method that does not include handpicking (e.g., a method in which B-lymphocytes are cultured and monoclonal antibodies are produced by limiting dilution).

The invention also provides methods of producing a monoclonal antibody. A monoclonal antibody is produced by providing a population of B-lymphocytes from a donor, immortalizing the population, separating a plurality of cells from the population to yield a first oligoclonal cell culture, culturing the cell culture in a culture medium and isolating the monoclonal antibody from the culture medium.

The population is immortalized by Epstein Barr Virus transformation, electrofusion, PEG fusion or gene transfection. Separation of a plurality of cells from the cell culture is repeated as desired (e.g., to yield a second, third, forth, fifth or greater oligoclonal cell culture). Additionally, a fusion is performed on the cell culture. Optionally, the oligoclonal cell culture is cloned, e.g. by limiting dilution, to produce a monoclonal cell culture.

In some aspects, the B-lymphocyte population is expanded prior to immortalization. Methods of expansion are known in the art and particular methods are described herein. For example, B-lymphocytes are expanded by stimulation with irradiated thymoma cells, e.g., EL4B5 cells; by stimulation of the lymphocytes with IL-4 and fibroblasts expressing human CD40L; by stimulation with CD3+CD28 activated Jurkat cell; or by stimulation of the lymphocytes with a mitogen, e.g., *Phaseolus vulgaris* Leukoagglutinin or pokeweed mitogen. Optionally, a plurality of B-lymphocytes are separated from the population of B-lymphocytes prior to immortalization to yield a first pre-immortalization B-lymphocyte cell culture. This separation step may be repeated as desired (e.g., to yield third, forth, fifth or greater pre-immortalization B-lymphocyte cell culture.

The donor is for example, a mammal, such as a human. To elicit antibody producing cells, the donor is vaccinated prior to providing the lymphocytes. Alternatively, the donor is exposed to a antigen or a pathogen of interest prior to providing the lymphocytes. Exposure to the antigen or pathogen of interest is natural or unintentional.

In a further aspect the invention provides a method of enriching a population of B-Lymphocytes for immunoglobin G (IgG) secretion by expanding the population and transforming the lymphocytes with an Epstein Barr Virus.

In some embodiments, the present methods will produce more stable populations of B-lymphocytes that produce antibodies that specifically bind a *Staphylococcus* or *Staphylococcus* antigen. The methods can also produce monoclonal antibodies that specifically bind a *Staphylococcus* or *Staphylococcus* antigen.

Also included in the invention are the stable B-lymphocytes and cultures thereof produced by the above methods and the antibodies produced by the stable B-lymphocytes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and from the claims.

DETAILED DESCRIPTION

Figure 1:
FIG. 1 is a photograph showing a clump of B-lymphocytes ready for handpicking.

The invention is based in part on the unexpected discovery that oligoclonal handpicking of immortalized B-lymphocytes results in increased survival and more stable antibody producing cultures.

Using traditional cloning techniques, after immortalization, high frequencies of B lymphocytes of cell fusion products die, stop proliferating or stop producing antibody. The invention provides methods that improve the survival and stability of cells after an immortalization procedure and therefore increase monoclonal antibody development. Repeated oligoclonal handpicking greatly enhances the frequency and yield of viable cells, proliferating cells, and antibody producing cells among those initially immortalized at least 10-fold compared to the viability of the parent culture and or the viability of cells obtained by traditional cloning techniques. Preferably, the yield of antibody producing cells is at least 10, 20, 30, 40, 50 60, 70, 80, 90, 100, 150, 200-fold (or more) greater than that of cells obtained by traditional cloning techniques or by cloning techniques that do not include the step of oligoclonal handpicking step described herein.

Many investigators have reported the development of human monoclonal antibodies in recent years (Masuho, Y. (1988) Infectious disease 2, 319-340 and James, K., Bell, G. T. (1987). Journal of Immunological Methods 100, 5-40.), but there are unsolved problems in the generation of human monoclonal antibodies remain unsolved. A common problem in human monoclonal antibody development is that certain immunizations are not allowed for ethical reasons, as they pose too great of a risk to immunize the individual. As a consequence almost all antibodies against naturally occurring antigens and government approved vaccines are developed from isolated human lymphocytes. The frequency of antigen-specific B-lymphocytes is very low. The results from in vitro immunization experiments with human lymphocytes have been very poor and not reproducible up till now (Borrebaeck, C. A. K. and Möller, S. A. (1986). Journal of Immunology 136, 3710-3715; Borrebaeck, C. A. K. (1989) Journal of Immunological Methods, 123, 157-165). In general, generation of human monoclonal antibodies has concentrated mainly on two methods: (i) fusion of lymphocytes with myeloma cells of murine, human and murine×human origin and ii) viral transformation of lymphocytes with Epstein-Barr virus (EBV).

Apart from the low fusion frequency inherent to the PEG-fusion technique, fusions with human lymphocytes are hampered for the reason that the ideal fusion partner has not yet been found. Partly because of that, the majority of human antibody producing hybridomas generated so far has shown to be unstable with respect to growth, life span and antibody production. By unstable is meant that the cells have a short lifespan, develop a limited or total lack of proliferation or lose the capacity to produce antibody. In contrast to the low immortalization frequency mentioned above, human B-lymphocytes are very efficiently immortalized by EBV. However, EBV-transformants grow poorly and attempts to fuse EBV-transformants with myeloma cells often failed due to problems with the stability of the resulting cell lines. In addition, typical EBV transformation results in monoclonal antibodies of the IgM class. In the present invention it was unexpectedly discovered that EBV transformation of B-lymphocytes that are in expansion results in a B-lymphocyte population that primarily produce antibodies of the IgG class.

The invention provides methods of producing a stable lymphocyte cell culture, B-cell or T-cell. A stable lymphocyte cell culture is produced by immortalizing a population of lymphocytes from a donor. A plurality of cells is separated from the population of immortalized cells by handpicking small clusters of cells, i.e., oligocloning. The clusters contain 5, 10, 20, 30, 40, 50 more cells. The separated plurality of cells is transferred to a new culture medium. Optionally, the handpicking is repeated 1, 2, 3, 4, 5, or more times until stabilization of the desired cells is achieved. Typically, after 2, 3, or more rounds of handpicking the cell culture is a monoclonal cell culture. If desired after stabilization of the culture, the cell culture is further cloned, for example by limited dilution cloning to yield a monoclonal cell culture and grown by standard methods. (Goding, *Monoclonal Antibodies: Principles and Practice*, Academic Press, (1986) pp. 59-103).

Handpicking is done manually or automatically. Manual handpicking is accomplished for example by visually inspecting the culture to identify clusters of cells. Cultures are visually inspected for example by using an inverted microscope or a stereo-loupe. Once identified the cluster or portion thereof is removed from the culture and is transferred to a new separate culture. Clusters are removed by any suitable method known in the art. For example, the clusters are removed using a pipette. Preferably, the clusters contains fewer than about 50 cells. For example, the clusters contain about 5 to 50 cells. Optionally, if the cell clusters contain greater than 50 cells only a portion of the cluster can be removed (i.e. about 5 to 50 cells). Automatic handpicking is accomplished for example by using an automated cloning machine such as the Elektra Cloning Device (Evotec) or ClonePix (Genetix). The automated cloning machine is set to pick a cluster of cells.

The culture medium in which the lymphocytes are cultured are assayed for the presence of antibodies directed against an antigen, i.e., pathogen such as disease-associated bacterium known in the art and described herein. The binding specificity of antibodies produced by the lymphocytes cells is determined by immunoprecipitation or by an in vitro binding assay, such as radioimmunoassay (RIA) or enzyme-linked immunoabsorbent assay (ELISA). Such techniques and assays are known in the art. The binding affinity of the antibody is be determined for example by the Scatchard analysis of Munson and Pollard, Anal. Biochem., 107:220 (1980), or determining the Ka or Kd on a Biacore.

In some embodiments, antibodies, e.g. monoclonal antibodies are isolated from the cell culture medium of the stable B-lymphocyte culture produced according to the present methods. Suitable culture media for this purpose include, for example, Dulbecco's Modified Eagle's Medium and RPMI-1640 medium. Alternatively, the cells can be grown in vivo as ascites in a mammal. The term "monoclonal antibody" (MAb), refers to a population of antibody molecules that contain only one molecular species of antibody molecule consisting of a unique light chain gene product and a unique heavy chain gene product. MAbs thus contain an antigen-binding site capable of immunoreacting with a particular epitope of the antigen characterized by a unique binding affinity for it. Methods of determining clonality are known in the art, such PCR sequencing of the immunoglobin gene of the cell. The monoclonal antibodies secreted by the cells are isolated or purified from the culture medium or ascites fluid by conventional immunoglobulin purification procedures such as, for example, protein A-Sepharose, hydroxylapatite chromatography, gel electrophoresis, dialysis, or affinity chromatography.

By stable lymphocyte cell culture is meant that the cell culture has a greater number (at least 10, 20, 50, 100, 200-fold greater) of viable, proliferating and/or antibody producing cells compared to an immortalized lymphocyte culture that has undergone traditional cloning (e.g., monocloning) such as limited dilution cloning. The improvement in the course of producing a more stable B-lymphocyte culture can also be expresses as a percent improvement relative to another culture as described herein. For example, the stable lymphocyte cell culture has 10%, 20%, 30%, 40%, 50% 75%, 85%, 90%, 95%, 100% (or more) viable, proliferating and/or antibody producing cell compared to an immortalized lymphocyte culture that has undergone traditional cloning. Alternatively or in addition, the improved characteristics is present when a cell or on average, cells within a population of cells, have a greater chance (at least 10, 20, 50, 100, 200-fold greater chance) of short-term (e.g., survival greater that 3 weeks) or long-term survival (e.g., survival greater that 10 weeks) compared to an immortalized lymphocyte that has undergone traditional cloning. The comparison can be relative to an immortalized B-lymphocytes or population of B-lymphocytes that has/have not been processes by a method including a handpicking step or that has or have undergone traditional cloning (e.g., cloning by limited dilution. For example, the cell is viable and/or productizing antibody 5, 10, 15, 20, 30, 40 or more weeks in a continuous culture. Viability, proliferation, survival and antibody production are measured by methods known in the art.

The donor is a mammal, such as a human or other primate, a rodent (including a rat or mouse), a horse, cow, dog, cat, pig, goat, sheep, lama, camel, dromedary, or rabbit. Alternately, the donor is a an avian such as a chicken, turkey, duck or goose. The donor is a reptile such as a snake, crocodile or turtle or a fish such a as a carp or a shark. Preferably, the donor is exposed to an antigen or pathogen of interest prior to providing the lymphocytes. In some embodiments, the donor has a cancer or has received a vaccination meant to mount an antibody response against a tumor or tumor associated antigen. In some embodiments the donor has mounted an antibody response to an autologous tissue or factors such as coagulation factors or cytokine. Alternatively, the donor has mounted an antibody response to an allogeniec tissue or factors such as Rhesus D antigen. Exposure to the antigen or pathogen of interest is natural, (i.e., infection) or artificial, (i.e., vaccination). An antigen is any substance that when introduced into a subject, e.g. mammal such as a human is capable of stimulating an immune response and/or the production of an antibody. A pathogen is an agent that causes a disease. Pathogens include, for example, a virus, a bacterium (whether gram-positive or gram-negative), a toxin, a toxin component, a fungus, and a parasite. Any inactivated (e.g., heat-killed) pathogen or any antigen(s) isolated either fully or partially there from, can be used to generate B-lymphocytes useful in the present methods. Tumor cells and tumor-associated antigens can also be used. Exemplary pathogens include a human immunodeficiency virus (i.e., an HIV of any clade), Rubella virus, a *bacillus* (e.g., *Bacillus anthracis*), *Rickettsia* (e.g., *R. prowazekii*, which is associated with epidemic typhus, *R. typhi*, which is associated with endemic typhus, and *R. rickettsii*, which is associated with spotted fever), a Variola virus, which is associated with small pox, *Clostridium* (e.g., *C. botulinum*: botulinum toxin is associated with botulism), *Staphylococcus* (e.g., *S. aureus, S. saprophyticus, S. haemolyticus, S. hominis* and *S. epidermidis*), *Streptococcus* (e.g., *S. pneumococci* and *S. pyogenes*), an influenza virus, including avian influenza viruses, *Escherichia* (e.g., *E. coli, E. adecarboxylata, E. albertii, E. blattae, E. fergusonii*, and *E. hermanni*), mycobacterium (e.g., *Mycobacterium tuberculosis, M. leprae, mycobacterium avium* complex, *M. kansasii* (usually associated with pneumonia or disseminated infection), *M. malmoense, M. simiae, M. szulgai, M. xenopi* (associated with pneumonia), *M. scrofulaceum* (associated with lymphadenitis), *M. abscessus, M. chelonae, M. haemophilum*, and *M. ulcerans* (skin and soft tissue infections)), *Salmonella* (e.g., *S. typhimurium* and *S. enteritidis*), *Helicobacter pylori, Francisella* (e.g., *F. novicida, F. philomiragia*, and *F. tularensis*), a Hepatitis virus (e.g., type A, B, C, D and E), vaccinia virus, a herpes simplex virus (e.g., HSV1 or HSV2), *Molluscum contagiosum, Cryptosporidium, Giardia lamblia* (this parasite is also known as *Giardia* intestinalis and *Giardia duodenalis*), any of the species of *Plasmodium* (particularly *P. falciparum, P. vivax, P. ovale*, and *P. malariae*), any parasitic species of the genus *Trypanosoma* (e.g., *T. brucei* and *T. cruzi*), *Pneumocystis* (e.g., *P. carinii* and *P. jiroveci*), the fungus *Tinea* (whether associated with *tinea pedis, tinea cruris*, or *tinea capitis*), or the fungus *Candida* (e.g., *Candida albicans*).

Exemplary antigens of interest, and the pathogens with which they are associated, are described further below.

*Staphylococcus*: *Staphylococcus* causes several diseases by various pathogenic mechanisms. The most frequent and serious of these diseases are bacteremia and its complications in hospitalized patients. In particular, *Staphylococcus* can cause wound infections and infections associated with catheters and prosthetic devices. Serious infections associated with *Staphylococcus* bacteremia include osteomyelitis, invasive endocarditis and septicemia. The problem is compounded by multiple antibiotic resistance in hospital strains, which severely limits the choice of therapy. In the majority of cases the causative organism is a strain of *S. aureus, S. epidermidis, S. haemolyticus* or *S. hominis*, or a combination of these.

It has been discovered that many clinically-significant isolates of *S. epidermidis, S. haemolyticus*, and *S. hominis* have in common an antigen, herein denoted "the antigen." The antigen represents the basis for a vaccine that provides protection against infection by a large number of clinically-significant *Staphylococcus* isolates. In this regard, a "clinically-significant" isolate is an isolate that is pathogenic.

The majority of *Staphylococcus* clinical isolates reacted very strongly with antigen/conjugate antibody sera, and thus were typeable as strains that contain the antigen. More particularly, typing of clinical isolates obtained from various sources has shown that approximately 60% of *S. epidermidis*, 50% of *S. haemolyticus* and 40% of *S. hominis* isolates express the antigen, as determined by slide agglutination. When enzymatic digests of the *S. haemolyticus* and *S. hominis* isolates were subjected to an immunodiffusion assay, all of the isolates tested positive for the presence of the antigen.

Antibodies to the antigen do not cross-react with polysaccharides isolated from any of *S. aureus* Type 5, Type 8, Type 4, or K73 (a Type 5 variant strain). The antigen therefore is specific, that is, it produces a single band only with antiserum from homologous strains.

The antigen can be obtained in recoverable amount, from certain *Staphylococcus* isolates cultured pursuant to the protocols described herein, in substantially pure form. In particular, purified antigen contains less than 1% nucleic acids. A "recoverable" amount in this regard means that the isolated amount of the antigen is detectable by a methodology less sensitive than radiolabeling, such as immunoassay, and can be subjected to further manipulations involving transfer of the antigen per se into solution.

*Botullinum* toxin: Botulin toxin is a neurotoxic protein produced by the bacterium *Clostridium botulinum*. It is the most poisonous naturally occurring substance in the world. A single drop is capable of killing 50,000 people. Though it is highly toxic, it is used in minute doses both to treat painful muscle spasms, and as a cosmetic treatment in some parts of the world. It is sold commercially under the brand names Botox and Dysport for this purpose. The terms Botox and Dysport are trade names and are not used generically to describe the neurotoxins produced by Clostridia species.

The heavy chain of the toxin is particularly important for targeting the toxin to specific types of axon terminals. The toxin must get inside the axon terminals in order to cause paralysis. Following the attachment of the toxin heavy chain to proteins on the surface of axon terminals, the toxin can be taken into neurons by endocytosis. The light chain is able to leave endocytotic vesicles and reach the cytoplasm. The light chain of the toxin has protease activity. The type A toxin proteolytically degrades the SNAP-25 protein, a type of SNARE protein. The SNAP-25 protein is required for the release of neurotransmitter substances from the axon endings. Botulin toxin specifically cleave these SNAREs, and so prevent neuro-secretory vesicles from docking/fusing with the nerve synapse plasma membrane and releasing their neurotransmitters

*Streptococcus pneumoniae*: Despite the name, the organism causes many types of infection other than pneumonitis, including acute sinusitis, otitis media, meningitis, osteomyelitis, septic arthritis, endocarditis, peritonitis, pericarditis, cellulitis, and brain abscess.

*S. pneumoniae* is the most common cause of bacterial meningitis in adults, and is one of the top two isolates found in otitis media. Pneumococcal pneumonia is more common in the very young and the very old.

*S. pneumoniae* can be differentiated from *Streptococcus viridans*, which is also alpha hemolytic, using an optochin test, as *S. pneumoniae* is optochin sensitive. The encapsulated, gram-positive coccoid bacteria have a distinctive morphology on gram stain, the so-called, "lancet shape." It has a carbohydrate capsule that is an important virulence factor for the organism. Because of the chemical make-up of the capsule (it is a polysaccharide) it will not cause an immune response in neonates and very young children (because they have not yet developed humoral immunity).

*S. pneumoniae* is normally found in the nasopharynx of 5-10% of healthy adults, and 20-40% of healthy children It can be found in higher amounts in certain environments, especially those where people are spending a great deal of time in close proximity to each other (day cares, army barracks). It attaches to nasopharyngeal cells through interaction of bacterial surface adhesins and epithelial cells. This normal colonization can become infection if the organisms are carried into areas, such as the Eustachian tube or nasal sinuses where it can cause otitis media and sinusitis, respectively. Pneumonia occurs if the organisms are inhaled into the lungs and not cleared (again, viral infection, or smoking-induced ciliary paralysis might be contributing factors). Once the organism makes its way to a site where it is not normally found, it activates the complement protein group, stimulates cytokine production, and attracts white blood cells (specifically neutrophils). The organism's polysaccharide capsule makes it resistant to phagocytosis, and if there is no preexisting anticapsular antibody, alveolar macrophages cannot adequately kill the pneumococci. The organism spreads to the blood stream (where it can cause bacteremia) and is carried to the meninges, joint spaces, bones, and peritoneal cavity, and may result in meningitis, brain abscess, septic arthritis, or osteomyelitis.

*S. pneumoniae* has several virulence factors, including the polysaccharide capsule that help it evade a host's immune system. It has pneumococcal surface proteins that inhibit activation of complement, and it secretes IgA1 protease that will destroy secretory IgA produced by the body.

The risk of pneumococcal infection is much increased in persons with impaired IgG synthesis, impaired phagocytosis, or defective clearance of pneumococci. In particular, the absence of a functional spleen, through congenital asplenia, splenectomy, or sickle-cell disease predisposes one to a more severe course of infection and prevention measures are indicated.

Human Immunodeficiency Virus (HIV): HIV is different in structure from previously described retroviruses. It is about 120 nm in diameter (120 billionths of a meter; around 60 times smaller than a red blood cell) and roughly spherical.

It is composed of two copies of positive single-stranded RNA enclosed by a conical capsid, which is in turn surrounded by a plasma membrane that is formed from part of the former host-cell membrane. Other enzymes contained within the virion particle include reverse transcriptase, integrase, and protease.

HIV has several major genes coding for structural proteins that are found in all retroviruses, and several nonstructural ("accessory") genes that are unique to it. The gag gene provides the physical infrastructure of the virus; pol provides the basic enzymes by which retroviruses reproduce; the env gene supplies the proteins essential for viral attachment and entry into a target cell. The accessory proteins tat, rev, nef; vif, vpr, and vpu enhance virus production. Although called accessory proteins, tat and rev transactivators are essential for virus replication.

In some strains of HIV, a mutation causes the production of an alternate accessory protein, Tev, from the fusion of tat, rev, and env.

The gp120 and gp41 proteins, both encoded by the env gene form gp160 before cleavage to two separate proteins, enable the virus to attach to and fuse with target cells to initiate the infectious cycle. Both, especially gp120, have been considered as targets of future treatments or vaccines against HIV.

The lymphocytes are peripheral blood lymphocytes. Alternatively, the lymphocytes are from the lymph node, spleen, bone marrow, tonsil, bursa of Fabricius or peyer's patch. Additionally, lymphocytes are isolated from abdominal, amniotic, articular, or pleural fluids. Lymphocytes are isolated from the donor by methods known in the art. For example, lymphocytes are isolated by Ficoll-paque.

The cells are immortalized by any method known in the art. For example, cell are immortalized by fusion, (e.g., electrofusion or exposure to polyethyleneglycol (PEG), transformation (e.g., viral transformation such as with Epstein Barr Virus (EBV) or retrovirus) or transfection (e.g., Notch1). Suitable cell fusion partners include murine or human myeloma cells such as NS-1, HuNS-1 or heteromyeloma cells such as K6H6B5 or PAI-1 cells.

Optionally, the lymphocytes are expanded prior to immortalizing the cell population. B-lymphocytes are expanded for example by stimulation with irradiated thymoma cells such as EL4/B5 cells (See, EP 0488470, the contents of which are hereby incorporated by reference in its entirety); irradiated CD154+ mouse fibroblasts (e.g. 3T6) and IL-4; irradiated activated Jurkat cells and IL-4 or CD40L (soluble, plate or cell bound) and optional an interleukin such as IL-4. (See, U.S. Pat. No. 6,297,052, and Banchereau, J. 1991, Nature 353:678-9, the contents of which are hereby incorporated by reference their entireties). Alternatively, the lymphocytes are expanded by stimulation with a mitogen such as *Phaseolus vulgaris* Leukoagglutinin or pokeweed mitogen.

In some embodiments, antibody producing lymphocytes are pre-selected prior to immortalization and/or expansion. By pre-selection is meant identification and separation or antigen or pathogen specific B-lymphocytes. Even in well-responding individuals, only a minor fraction of the lymphocytes is able to produce antibodies of desired specificity. Therefore, preselection of antibody producing B-cells, results in more efficient immortalization techniques and avoids laborious screening of very large numbers of supernatants resulting from fusion, electrofusion, or clonal expansion of the cells. Preselection of antibody producing B-cell is accomplished by methods known in the art. For example, panning, rosetting, fluorescence activated cell sorting (FACS), or paramagnetic immunobeads.

In other embodiments, oligoclonal handpicking and/or propagation of lymphocytes is performed during lymphocytes expansion and or prior to immortalization. By propagation is meant the transfer of a portion of the culture to a new culture thereby expanding the number of cells.

Also included in the invention are the stable B-cell cultures and monoclonal antibody or fragments thereof produced by the methods described herein. Optionally the monoclonal antibody is coupled (i.e., physically linked) to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$. Alternatively, the monoclonal antibody is coupled to a chemotherapeutic agent; a toxin (e.g., an enzymatically active toxin of bacterial, fungal, plant, or animal origin, or fragments thereof); a radioactive isotope (i.e., a radioconjugate). Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes.

The antibodies of the invention can be incorporated into pharmaceutical compositions suitable for administration. Such compositions typically comprise the antibody, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, intramuscular, intraperitoneal, intravenous, subcutaneous, intranasal, epidural, transdermal (topical), transmucosal, rectal administration and oral routes. The Therapeutics of the present invention may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

In keeping with the summary provided here and in accordance with the more detailed description certain embodiments of the invention set out in the paragraphs immediately below.

A method of producing a stable B-lymphocyte cell culture, by providing a population of B-lymphocytes from a donor; immortalizing the population; separating a plurality of cells from the population to yield a first oligoclonal cell culture; and culturing the oligoclonal cell culture thereby producing a stable B-lymphocyte cell culture. The method further includes expanding the population prior to immortalizing the population to yield an expanded population of B-lymphocytes and or separating an antigen or pathogen of interest specific B-lymphocytes from non-antigen or pathogen of interest specific B-lymphocytes in the population prior to immortalizing the population to yield an enriched population of B-lymphocytes. Optionally the method includes separating a plurality of cells from the population to yield a first pre-immortilation B-lymphocyte cell culture and or separating a plurality of cells from the first pre-immortilization B-lymphocyte cell culture to yield a second pre-immortilization B-lymphocyte cell culture.

The population is expanded by stimulation of the lymphocytes with irradiated thymoma cells such as EL4B5 cells. Alternatively, the population is expanded by stimulation of the lymphocytes with CD40L and IL-4, CD3+ CD28 activated Jurkat cells or a mitogen such as *Phaseolus vulgaris* Leucoagglutinin or pokeweed mitogen.

The donor is vaccinated for a pathogen of interest or a tumor associated antigen prior to providing the a sample comprising a population of lymphocytes or the donor is naturally or unintentionally exposed to a pathogen of interest or a tumor associated antigen prior to providing the lymphocytes. The donor is a human The population is immortalized by Epstein Barr Virus transformation, electrofusion, PEG fusion or gene transfection. The method further includes cloning the stable B-lymphocyte cell culture to yield a monoclonal cell culture. Cloning is for example by limited dilution cloning.

The method further includes separating a plurality of cells from the first oligoclonal cell culture to yield a second oligoclonal cell culture and or separating a plurality of cells from the second oligoclonal cell culture to yield a third oligoclonal cell culture. Optionally, cell fusion on the monoclonal cell culture is performed.

Also provide by the invention is a method of producing a monoclonal antibody by providing a population of B-lymphocytes from a donor; immortalizing said population separating a plurality of cells from the population to yield a first oligoclonal cell culture; culturing the cell culture in a culture medium; and isolating the monoclonal antibody from said culture medium. The method further includes cloning the cell culture prior to step isolating the monoclonal antibody to produce a monoclonal cell culture in the event that the oligoclonal culture does not produce monoclonal antibodies The cloning is by limited dilution cloning. Optionally, the method includes expanding the population prior to immortalizing the population. The population is expanded by stimulation of the lymphocytes with irradiated thymoma cells such as EL4B5 cells. The population is expanded by stimulation of the lymphocytes with CD40L and IL-4 or CD3+ CD28 activated Jurkat cells or a mitogen such as *Phaseolus vulgaris* Leucoagglutinin or pokeweed mitogen. The donor is vaccinated prior to providing the lymphocytes.

The method further includes separating pathogen of interest or tumor associated antigen specific B-lymphocytes from non-pathogen of interest or tumor associated antigen specific B-lymphocytes in the population prior to immortalizing the population. The method also includes separating a plurality of cells from the population to yield a first B-lymphocyte cell culture. The donor is exposed to a pathogen of interest or tumor associated antigen prior to providing the lymphocytes. The donor is a human. The population is immortalized by Epstein Barr Virus transformation, electrofusion, PEG fusion or gene transfection. Optionally the method includes cloning the oligoclonal cell culture to yield a monoclonal cell culture. The cloning is limited dilution cloning. comprising separating a plurality of cells from the first oligoclonal cell culture to yield a second oligoclonal cell culture and separating a plurality of cells from the second oligoclonal cell culture to yield a third oligoclonal cell culture.

The invention further provides a method of enriching a population of isolated B-Lymphocytes for immunoglobulin type G (IgG) secretion by expanding the lymphocytes and transforming the lymphocytes with an Epstein Barr Virus.

In a further aspect the invention provides a method of producing a stable B-lymphocyte cell culture, wherein one or more B-lymphocytes within the culture produces anti-Staphylococcus antibodies, by providing, from a donor who has been exposed to *Staphylococcus* or one or more *Staphylococcus* antigens, a sample comprising a population of B-lymphocytes; immortalizing B-lymphocytes within the population of B-lymphocytes; separating a plurality of cells from the population of B-lymphocytes to yield a first oligoclonal cell culture; and culturing the oligoclonal cell culture thereby producing a stable B-lymphocyte cell culture comprising B-lymphocytes that produce anti-Staphylococcus antibodies. The *Staphylococcus* is *Staphylococcus aureus* or *Staphylococcus epidermidis*.

The method further includes expanding the population of B-lymphocytes thereby producing an expanded population of B-lymphocytes prior to immortalizing the population; expanding by stimulating the population of B-lymphocytes with irradiated thymoma cells such as EL4B5 cells or expanding by stimulating the population of B-lymphocytes with CD40L and IL-4; CD3+ CD28 activated Jurkat cells; or a mitogen such as *Phaseolus vulgaris* Leucoagglutinin or pokeweed mitogen. Optionally the method further includes enriching the B-lymphocytes in the sample or the expanded population of B-lymphocytes or selecting B-lymphocytes in the sample or the expanded population of B-lymphocytes, wherein selecting comprises separating a plurality of B-lymphocytes that produce antibodies that specifically bind a *Staphylococcus* antigen from B-lymphocytes that do not produce antibodies that specifically bind the *Staphylococcus* antigen and or separating a plurality of cells from the population of B-lymphocytes prior to immortalizing B-lymphocytes within the population of B-lymphocytes to yield a first pre-immortalization oligoclonal cell culture.

The donor is vaccinated against a *Staphylococcus* bacterium prior to providing the sample containing a population of B-lymphocytes. The donor is unintentionally exposed to a *Staphyloccus* bacterium prior to providing the sample comprising a population of B-lymphocytes. The donor is a human. Immortalizing B-lymphocytes includes Epstein Barr Virus transformation, electrofusion, PEG fusion, or gene transfection. Optionally the method further includes cloning cells within the stable B-lymphocyte cell culture to yield a monoclonal cell culture. The method further includes separating a plurality of cells from the first oligoclonal cell culture to yield a second oligoclonal cell culture and, optionally, separating a plurality of cells from the second oligoclonal cell culture to yield a third oligoclonal cell culture an/or separating a plurality of cells from the first pre-immortalization oligoclonal cell culture to yield a second pre-immortalization oligoclonal cell culture and, optionally, separating a plurality of cells from the second pre-immortalization oligoclonal cell culture to yield a third pre-immortalization oligoclonal cell culture. Optionally a cell fusion is performed on any resulting monoclonal cell culture.

In a further aspect the invention provides a method of producing a monoclonal antibody that specifically binds a *Staphylococcus* antigen, the method by providing, from a donor who has been exposed to *Staphylococcus* or one or more *Staphylococcus* antigens, a sample comprising a population of B-lymphocytes; immortalizing B-lymphocytes within the population of B-lymphocytes; separating a plurality of cells from the population of B-lymphocytes to yield a first oligoclonal cell culture; culturing the oligoclonal cell culture in a culture medium; and isolating the monoclonal antibody from the culture medium. The method further includes, in the event the oligoclonal cell culture does not produce monoclonal antibodies, cloning the oligoclonal cell culture prior to step isolating the monoclonal antibody. The cloning is by limited dilution cloning.

The invention further includes method of enriching a population of isolated B-lymphocytes that produce antibodies that specifically bind a *Staphylococcus* antigen for immunoglobulin type G (IgG) secretion, the method comprising expanding the B-lymphocytes and transforming the B-lymphocytes with an Epstein Barr Virus.

The invention also includes a stable B-lymphocyte cell culture and or a monoclonal antibody produced by the methods described herein The monoclonal antibody is linked to a detectable label or a toxin. Also included are composition contain on or more monoclonal antibodies.

The invention will be further illustrated in the following non-limiting examples.

Example 1

General Methods

Reagents

Culture medium DMEM/HAM's F12 (Cambrex Biosciences 12-719F) is prepared with 1300 mg/l sodium bicarbonate (Merck), 55 mg/l sodium pyruvate (Fluka), 2.3 mg/l 2-mercaptoethanol (Merck). 60 mg/l Gentamycin (Sigma), and 8% Fetal Bovine Serum (Wisent). In fusion experiments, the medium is further supplemented with 13.61 mg/l hypoxanthine (Fluka) and 3.83 mg/l thymidine (Fluka). This medium is referred to as DMEM/HAM's F12/HT.

Selection of hybridomas is performed in DMEM/HAM's F12/HT supplemented with 0.0004 mM aminopterin (Sigma) and optionally 1% of IL-6 containing supernatant of a human bladder carcinoma cell line T24 (T24CM). The selection medium is referred to as HAT-medium. Fusion medium: Ready to use hypo-osmotic buffer (Eppendorf AG)

Cell Cultures

Mutant EL-4 thymoma cells, EL-4/B5 are routinely cultured in DMEM/HAM's F12 supplemented with 8% FCS) at cell concentrations between $1\times10^4$ to $1\times10^6$ c/ml. If the cells exceed a density $1\times10^6$ cells/ml, they may lose their B-cell stimulating activity. Murine myeloma cells (SP2/0, ECACC# 85072401), human myeloma cells (HuNS-1, ATCC® # CRL-8644), or xenohybrids (K6H6B5 (ATCC® # CRL-1823) and PAI-1 (ATCC®# HB-8654)) were used as fusion partners for murine and human B-cells respectively. The cells are routinely cultured in DMEM/HAM's F12/HT medium supplemented with 10% FCS at concentrations between $5\times10^4$ and $15\times10^5$ cells/ml. One day before fusion, cultures were split 1:3 to create a log-phase culture on the day of fusion.

Preparation of Human T-Cell/Macrophage Supernatant (TSN)

Freshly isolated mononuclear cells were centrifuged for 10 minutes at 2000 N/kg. Subsequently, B-cells and T-cells were separated according to a modification of the method described by Gutierrez et al. (*J Immunol Methods*. 1979; 29(1):57-63). The pellet was resuspended in 5 ml of a mixture of 0.5 ml 1.5M NaCl and 4.5 ml Isopaque-Percoll (100% SIP) Then, a 10 ml layer of 70% SIP followed by a 25 ml layer of 50% SIP were layered onto the 100% SIP. The gradient was centrifuged for 10 min. at 25,000 N/kg. The enriched T-cell fraction remaining at the interface between 70% and 50% SIP is collected and washed twice with DMEM/HAM's F12 supplemented with 10% FCS. Washed cells are stimulated for 40-45 hours in DMEM/HAM's F12 supplemented with 10% FCS, 5 g/ml PHA (Wellcome) and 10 ng/ml PMA (Sigma). Finally, supernatant is harvested, filtered through a 0.2 µm membrane filter and stored in aliquots at −70° C.

EL-4/5B-Cell Cultures

EL-4/5B-cell cultures are prepared as described by Zubler et al (*J Immunol*. 1985 June; 134(6):3662-8.) Briefly, crude or purified B-cells are mixed with TSN and about 50,000 irradiated (2500 RAD) EL-4/B5-cells in a final volume of 200 ml DMEM/HAM's F12 supplemented with 10% FCS in 96-well flat bottomed tissue culture plates. The optimal amount of TSN is established for each batch by titration. Usually 10% TSN was sufficient for optimal stimulation of human B-cells whereas 20% TSN is usually required for murine B-cells. The cultures are incubated at 37° C., with 5% CO2 and 100% humidity. Between Day 8 and Day 12 after exposure to TSN and thymoma cells, supernatants were tested for immunoglobulin production.

3T6.CD40L Cultures

Briefly, 3T6.CD40L cells are cultured to 80% confluence in RPMI1640 supplemented with 5% Fetal Bovine Serum, genetecin (200 ng/mL), and 2.3 mg/l 2-mercaptoethanol (Merck) at 37° C., 5% $CO_2$, with 100% humidity for 3-4 days. The culture medium is discarded and the cells are treated with EDTA (6 ml in T75 or 3 ml in T25). The cells are then re-suspended in Hanks Balanced Salt Solution (HBBS) and irradiated with 100 Gy from a Cs137 source. The cell are washed in linolea medium, counted and frozen in liquid nitrogen until use.

Isolation of Mononuclear Cells

Blood was drawn from an Anthrax vaccinee, 7 days after the latest booster injection, or blood from a healthy volunteer never having been exposed to *S pneumoniae*. The blood was diluted 50/50 v/v with sterile PBS and spun down on Isopaque Ficoll (45 minutes. 400×g). The mononuclear cells resulting from this procedure were either used fresh, or frozen into liquid $N_2$.

Enrichment of Human B-Cells

The isolated mononuclear cells (fresh or thawed) were enriched for B lymphocytes with 'untouched B cell' protocol of an AutoMACS apparatus (Miltenyi Biotec Inc. Auburn, Calif.). These enriched B cell suspensions (greater than 95%) were used either fresh or thawed from liquid $N_2$.

CD40 Expansion of Lymphocytes

Enriched B-lymphocytes are expanded using 3T6CD40L cell based expansion system. Briefly, 3T6CD40L cells were harvested at ~80% confluence. The culture medium was discarded and EDTA buffer was added (6 ml in T75 or 3 ml in T25). The cells were resuspended and irradiated with 100 Gy with a Cs137 source. The cells are then washed in linolea medium and counted. When plated in 24-well plates the cell concentration was about $8\times10^4$ ml; when plated in 96 wells the cell concentration was about $2\times10^5$/ml. A similar amount and volume of B cells are added to the to irradiated 3T6CD40L cells (i.e., the B-cell: 3T6CD40L cell ratio was about 1:1). 10 ng/ml rhIL-4 was added to the culture.

The culture medium was refreshed, by replacing about half of the medium+IL-4 every 3 days. Every 7 days freshly irradiated 3T6CD40L cells ($2\times10^5$ in 24 wells; $5\times10^3$ in 96 wells) were added or B cells were harvested and transferred to new plate with freshly irradiated 3T6CD40L cells at the same concentration used to start the culture). After ~5 to 7 days characteristic B cell clumps were visible in culture. Cultured B cells were harvested between days 5 and 11 by carefully resuspending the cells with a Pasteur pipette.

Jurkat Supported Expansion of Lmphocytes

Enriched B-lymphocytes are expanded using an expansion system consisting of activated Jurkat cells and IL-4. Briefly, Jurkat cells are cultured at 37° C., 5% $CO_2$ and 100% humidity in DMEM/F12 medium supplemented with 8% Fetal Bovine Serum, 60 mg/mL Gentamycin, and 2.3 mg/ml mercaptoethanol. The Jurkat cells are subsequently incubated with 0.1 mg/mll CD3 and 1.0 mg/mlCD28 monoclonal antibody according to standard procedures [Cook 2002, J. Immunol. 169:254-60, Thomas 2002, Clin Immunol 105:259-72]. Jurkat cells are irradiated (3.0 Gy from a Cs137 source) and after irradiation, Jurkat cells B lymphocytes are mixed in ratio's from 1:10 to 10:1 and 10 ng/ml rhIL-4 is added.

Oligoclonal Handpicking Procedure

A 6, 12, 24, or 96-well flat-bottom cell culture plate or petri dish containing a cell culture (either expanding primary B cell populations or fusion products) in liquid culture medium is put under an inverted microscope or stereo-loupe (magnification 40× or 100×). The cultures were assessed under the microscope for the presence of cell clumps of 5-50 or 50->100 cells. When such clumps were present, the culture plate or dish was opened for hand-picking. An example of such cell clump is shown in FIG. 1. Guided by the microscope, a sterile glass pipette with a small opening or a similar instrument was introduced into the cell culture and brought in proximity of a cell clump of interest. The cell clump (5-50 cells), or part of it (50->100) was then sucked into the pipette tip, taken out of the plate and gently introduced into a well of a new 96-well plate containing 100-200 µL of the culture medium fit for the cell population in question. This procedure was repeated until the harvested well, plate or dish was exhausted. Every hand-picked cell clump is transferred to an individual well, no clumps are pooled. This procedure can be repeated many times, but is usually performed 1-3 times.

Oligoclonal handpicking is performed in different ways and by using different instruments. A number of examples are described below:

Example 1. The instrument is a glass pipette (Pasteur pipette) which is stretched in a flame to make both the tip and the opening thinner. The elongated glass pipette is operated by manipulating a small pipette bulb on the distal part Example 2. The instrument is the same as the pipette used in example 1, but now it has a short, thin and non-elastic tube attached to the distal part. The free end of the tube has a mouth piece on it which is plugged with sterile cotton wool. The instrument is operated by applying minimal suction and pressure by the mouth.

Example 3. The instrument and tubing is the same as in Example 2, but now it operated by an electronic micro-pipettor, or a pipettor or syringe that operates a fixed volume per click. The volume can be set at 10-25 µL.

Example 4. The instrument is a small piece of thin, transparent not too flexible tube attached to a normal glass pipette or any of the operating tools of Examples 2 and 3.

Example 5. The process is fully automated eg. by using an automated cloning machine set to transfer clumps of cells in stead of transferring approximately 1 cell at a time.

Panning Procedure

Six-well culture plates were incubated overnight with 4 ml per well of a solution containing 1 to 10 µg antigen in 0.05 M sodiumcarbonate buffer pH=9.6. Subsequently, the wells were washed with PBS and the plates were directly used for panning experiments or stored at −20° C. Panning was performed by incubating enriched B-cells on antigen coated wells for 1 to 2 hours at 37° C., 5% $CO_2$ and 100% humidity. After this incubation, the unattached cells were removed gently by three subsequent washes with PBS. The antigen-bound, specific B-cells were then recovered by incubating each well with 250 ul PBS containing 1.1 mM sodium EDTA and 0.05% trypsin (Flow, cat no. 16-893-49) pH=7.5 for 2 minutes. Trypsin treatment was stopped by addition of 5 ml DMEM/HAM's F12 supplemented with 10% FCS. Optionally, the entire surface of one or more wells was flushed with the medium using a Pasteur pipette in order to remove residual attached B-cells mechanically.

Electrofusion

Electrofusion of lymphocytes to K6H6/B5 myeloma cells occurs in a ratio's ranging from 1:0.5 to 1:10 in 60 µl of fusion medium in a micro chamber. B-cell cultures were mixed myeloma cells in 2-ml centrifuge tubes. The cells were rendered serum-free by washing once with fusion medium. Then, the cell suspension was then centrifuged and the pellet was resuspended in 60 µl fusion medium at room temperature. The complete cell suspension was pipetted into the internal space of a fusion chamber consisting of two stainless steel, disc-shaped electrodes embedded in a Perspex™ box. The electrodes are separated by a Teflon™ spacer of varying diameter and 0.50 mm thickness. Alignment occurs by an alternating electric field of 1 MHz and 150 V/cm for 30 seconds, immediately followed by a peek pulse of 1500 V/cm for 15 µs Then, immediately a square, high field pulse of 3 kV/cm and 10 second duration was applied causing cell membrane breakdown. The alternating field was applied again for 30 seconds in order to allow intermingling of cells and resealing of membranes. The contents of the fusion chamber were transferred to 20 ml selection medium (HAT) and plated into a 96-well microculture plate. At Day 9, the cultures were examined for hybridoma growth and the supernatants were tested for immunoglobulin production.

PEG Fusion:

PEG fusion to K6H6/B5 myeloma cells occurs in a 1:1 ratio in 1-1.5 ml PEG 4000 (50%) solution for 3 minutes. After a washing step with DMEM/F12 these fusion products were cultured overnight in 100 µl HT medium. The next day, 100 µl of HT medium supplemented with 0.0008 mM amiopterin is added to the culture. The fusion products are cultured in this selection medium (HAT) for 9 days.

Example 2

EBV Transformation of Enriched Human B-Cells Isolated from an Anthrax-Vaccinated Donor Results in the Generation of a Stable B-Cell Culture Specific for Protective Antigen (PA)

Enriched B-cells from an Anthrax vaccinated donor were used to produce a stable B-cell culture producing monoclonal antibodies for Protective Antigen. In four independent experimental protocols as outlined below enriched B-cell isolated were seeded on 24 well plates with 3T6.CD40L cells.

Protocol 1: Cells (5,000-10,000) were cultured on 100,000 3T6.CD40L cells/well in a 24 wells plate. Cells were EBV transformed immediately, by incubating with an adequate EBV stock. The EBV supernatant was replaced by standard growth medium plus IL-4 (10 ng/mL) after 2.5 hours. The B-cells were cultured in this medium for 2 to 3 weeks.

Protocol 2: Cells (5,000-10,000) were cultured on 100,000 3T6.CD40L cells/well in a 24 wells plate and expanded for 3 days before EBV transformation. The EBV supernatant was replaced by standard growth medium plus IL-4 (10 ng/mL) after 2.5 hours. The B-cells were cultured in this medium for 2 to 3 weeks.

Protocol 3: Cells (200,000 c/w) were panned on a plate coated with PA for 2 hrs, and subsequently, 100,000 3T6.CD40L cells were added per well to the panned B cells in a 24 wells plate. B-Cells were EBV transformed immediately, by incubation with an adequate EBV stock. The EBV supernatant was replaced by standard growth medium plus IL-4 (10 ng/mL) after 2.5 hours. Cells were cultured in this medium for 2 to 3 weeks.

Protocol 4: Cells (200,000 c/w) were panned on a plate coated with PA for 2 hrs. Subsequently, 100,000 3T6.CD40L cell with IL-4 were added to each well to the panned B cells in a 24 wells plate for a 3 day expansion after which EBV transformation followed. The EBV supernatant was replaced by standard growth medium plus IL-4 (10 ng/mL) after 2.5 hours. Cells were cultured in this medium for 2 to 3 weeks. Passage of the cultured cells occurred based on growth characteristics.

After culturing for 2-3 weeks a PA-ELISA was performed on each of the cultures. (Any indirect ELISA protocol can be used. Here the PA concentration was 0.5 µg/mL, development with TMB).

Results:

All wells demonstrated cell growth. Protocol 1 demonstrated 4 anti-PA-producing wells, Protocol 2 demonstrated 1, Protocol 3, showed 12, and Protocol 4 showed 8 anti-PA-producing wells. Clearly, Protocols 3 and 4 resulted in a higher frequency of anti-PA-antibody producers. In addition, these protocols talso demonstrated higher OD's upon ELISA. This experiment shows that panning prior to immortalization can be a tool to enrich for specific antibody producing B lymphocytes.

Cell cultures grown according to Protocol 3 were used further. The wells with the highest positive score for anti-PA antibody production were seeded in microtiter plates (1, 10 and 100 cell/well) on 3T6.CD40L cells. The wells were screened for anti-PA antibody production, and wells scoring positive were handpicked as described above and screened for anti-PA antibodies three times (except the 1 cell/well seeding). The results are shown in Table 1.

TABLE 1

Cell lines producing anti-PA-antibody:

1 c/w: 6/1760 = 0.3%
10 c/w: 50/840 = 5.9%
100 c/w: 57/652 = 8.7%

Five positive (oligo)clones were grown and, checked for anti-PA antibody production, and cultured in a 12 well plate, then in a 6 well plate, and finally in a 25 cm² culture flask. After having grown the cells to confluence, part was frozen, and another part (the part with the highest turnover rate and production levels) was PEG-fused with K6H6/B5. After fusion, the cells were cultured in selection medium (HAT 9 for days, HT for 5 days) and cloned. The generated hybridomas were screened by PA ELISA, and the best (based on proliferation and production) were re-cloned. Five hybridomas were generated.

Example 3

Handpicking of Fused Enriched Human B-Cells Isolated from Anthrax Vaccinated Donor Results in of Production Antigen Specific Stable B-Cell Cultures Enriched B-cells from an Anthrax vaccinated donor were panned as described above in a 6 wells plate coated with the desired antigen (Ag) Unbound cells were washed away and discarded, bound cells were removed from the plate by trypsin treatment (Protocol 1) or were left on the plate (Protocol 2).

Protocol 1. Trypsin treated cells (1,000-1,500 cell per well) were added to 96-wells microtiter plates having 10,000 3T6.CD40L cells/well and IL4 (10 ng/mL). After 3 days of expansion, the wells were tested for anti-Ag antibody production. Cells from wells scoring positive for antibody were fused to K6H6/B5 myeloma cells in a 1:1 ratio. Fusion either occurred by electrofusion or PEG fusion as described above). After the fusion, the fusion products are seeded into microtiter plates in a density of 10,000-20,000 cells/well and left in HAT medium for 9 days, followed by HT medium for 4-6 days and then complete growth medium. Cells are tested for growth and anti-Ag antibody production after the first 9 days (upon HAT to HT change). Antibody Positive wells are then handpicked, grown for 3 days, screened, handpicked again, for a total of at least 3 times. After the handpicking the cells were cloned with an initial density of 1 cell/well.

Protocol 2. 3T6.CD40L cells (500,000 cells/well) and IL-4 (10 ng/mL) were added to the panned cells stuck to the plate. After 3 days of expansion, the wells were tested for growth and anti-Ag antibody production. Wells scoring positive were handpicked onto new 3T6.CD40L cells plus IL-4 in microtiter plates, allowed to expand for another 3 to 5 days, and screened for anti-Ag antibody production. Wells scoring positive were then fused K6H6/B5 myeloma cells in a 1:1 ratio. Fusion either occurred by electrofusion or PEG fusion. After the fusion, the fusion products are seeded into microtiter plates in a density of 10,000-20,000 c/w and left on HAT medium for 9 days, HT medium for 4-6 days and then complete growth medium. Cells are tested for growth and anti-Ag Ab production after the first 9 days (upon HAT to HT change). Positive wells are then handpicked, grown for 3 days, screened, handpicked again, for a total of at least 3 times. After handpicking the cells are cloned with an initial density of 1 cell/well. The results are shown in Table 2.

TABLE 2

| | Growing hybridomas | IgG producing hybridomas | Specific Ab-producing hybridomas |
|---|---|---|---|
| Protocol1 electrofusion | 54/264 | 26/54 | 4/26 (15%) |
| Protocol 2 electrofusion | 67/264 | 48/67 | 15/48 (31%) |
| Protocol PEG fusion | 547/1584 | 547/547 | 125/547 (23%) |
| Protocol PEG fusion | 101/192 | 100/101 | 26/100 (26%) |

Example 4

Human Monoclonal Antibodies Against Botulinum Toxin A

Enriched B lymphocytes from a Botulinum toxoid vaccinated donor were used to generate stable B cell hybridoma cultures producing monoclonal antibodies recognizing Botulinum toxoid A. In 4 independent protocols as outlined below enriched B cells were seeded in 24 or 96 well plates with rhIL-4 (10 ng/mL) and irradiated 3T6.CD40L or Jurkat cells for a period of 5-12 days. Fresh rhIL-4 was added every forth day. A Botulinum toxoid ELISA was used to screen for positive wells.

Protocol 1. Enriched B lymphocytes and rhIL-4 were added to irradiated 3T6.CD40L cells. After expansion, B cells were immortalized by PEG fusion with K6H6B5 myeloma cells. After immortalization, cells were seeded into 96-well plates at a density of 10,000-20,000 c/w and left on HAT medium for 9 days, transferred to HT medium for 7 days, and were thereafter cultured in complete growth medium. Positive wells were handpicked, grown for 4-7 days, screened and handpicked again for a total of 2-3 times. After handpicking the cells are cloned with an initial density of 1 cell/well.

Protocol 2. Protocol 2 was identical to protocol 1, except that, but with the addition of anyone or a combination of the following factors: B cell activating factor (BAFF), a proliferation-inducing ligand (APRIL) or *Staphylococcus aureus* enterotoxin A (SEA) to the cells during the expansion.

Protocol 3. Protocol 3 was identical to protocol 1 but CD3+ CD28 activated Jurkat cells were used instead of 3T6.CD40L cells.

Protocol 4. Enriched B lymphocytes and rhIL-4 were added to irradiated 3T6.CD40L cells. After 5-8 days, B cell clumps were handpicked from the 3T6.CD40L cells, seeded onto fresh 3T6.CD40L cells and expanded for another 3-5 days (for a total of 1-3 times). Positive wells were handpicked again and immortalized by electrofusion or PEG fusion. After immortalization, cells were seeded into 96-well plates and left on HAT medium for 9 days, followed by HT medium for 7 days, and are thereafter cultured on complete growth medium. Positive wells were handpicked, grown for 4-7 days, screened, handpicked again for a total of 2-3 times. After handpicking the cells are cloned with an initial density of 1 cell/well.

Example 5

Human Monoclonal Antibodies Against *Staphylococcus aureus* Polysaccharide Type 5

Protocol 1. Enriched B lymphocytes and rhIL-4 were added to irradiated 3T6.CD40L cells. After expansion, B cells were immortalized by PEG fusion with K6H6B5 myeloma cells. After immortalization, cells were seeded into 96-well plates at a density of 10,000-20,000 cell/well and left on HAT medium for 9 days, followed by HT medium for 7 days, and are thereafter cultured on complete growth medium. Positive wells were handpicked, grown for 4-7 days, screened, handpicked again for a total of 2-3 times. After handpicking the cells are cloned with an initial density of 1 cell/well.

Protocol 2. Enriched B lymphocytes and rhIL-4 were added to irradiated 3T6.CD40L cells. After expansion, B cells were immortalized by electrofusion with K6H6B5 myeloma cells. After immortalization, cells were seeded into 96-well plates at a density of 10,000-20,000 cells/well and left on HAT medium for 9 days, followed by HT medium for 7 days, and were thereafter cultured on complete growth medium. Positive wells were handpicked, grown for 4-7 days, screened, handpicked again for a total of 2-3 times. After handpicking the cells are cloned with an initial density of 1 cell/well.

Protocol 3. Enriched B-lymphocytes and rhIL-4 were added to irradiated 3T6.CD40L cells. After 5-8 days, B cell clumps were handpicked from the 3T6.CD40L cells and immortalized by electrofusion or PEG fusion. After immortalization, cells were seeded into 96-well plates and left on HAT medium for 9 days, followed by HT medium for 7 days, and were thereafter cultured on complete growth medium. Positive wells were handpicked, grown for 4-7 days, screened, handpicked again for a total of 2-3 times. After handpicking the cells are cloned with an initial density of 1 cell/well.

Other embodiments are within the following claims.

What is claimed is:

1. A method of producing a monoclonal antibody, comprising
   a) providing a population of B-lymphocytes from a donor;
   b) immortalizing said population;
   c) handpicking a cluster of B-lymphocytes from said population to yield a first oligoclonal cell culture, wherein said cluster comprises 5-50 or 50-100 B-lymphocytes;
   d) culturing said cell culture in a culture medium;
   e) cloning said cell culture to produce a monoclonal cell culture;
   f) isolating a monoclonal antibody from said monoclonal cell culture; and
   g) determining the binding specificity of said monoclonal antibody.

2. The method of claim 1, wherein said cloning is by limited dilution cloning.

3. The method of claim 1, further comprising expanding the population prior to step b).

4. The method of claim 3, wherein the population is expanded by stimulation of the lymphocytes with irradiated thymoma cells.

5. The method of claim 4, wherein the thymoma cells are EL4B5 cells.

6. The method of claim 3, wherein the population is expanded by stimulation of the lymphocytes with CD40L and IL-4, or CD3+CD28 activated Jurkat cells.

7. The method of claim 3, wherein the population is expanded by stimulation of the lymphocytes with a mitogen.

8. The method of claim 7, wherein the mitogen is *Phaseolus vulgaris* Leucoagglutinin or pokeweed mitogen.

9. The method of claim 1, wherein the donor is vaccinated prior to providing the lymphocytes.

10. The method of claim 1, wherein the donor is exposed to a pathogen of interest or tumor associated antigen prior to providing the lymphocytes.

11. The method of claim 1, wherein the donor is a human.

12. The method of claim 1, wherein the population in step b) is immortalized by Epstein Barr Virus transformation, electrofusion, PEG fusion or gene transfection.

13. The method of claim 1, further comprising handpicking a cluster of cells from the first oligoclonal cell culture to yield a second oligoclonal cell culture prior to step e) and culturing said second oligoclonal cell culture in a culture medium, wherein said cluster comprises 5-50 or 50-100 B-lymphocytes.

14. The method of claim 13, further comprising handpicking a cluster of cells from the second oligoclonal cell culture to yield a third oligoclonal cell culture prior to step e) and culturing said third oligoclonal cell culture in a culture medium, wherein said cluster comprises 5-50 or 50-100 B-lymphocytes.

15. The method of claim 1, further comprising separating antigen specific B-lymphocytes that are specific for the pathogen of interest or the tumor associated antigen from B-lymphocytes that are not specific for the pathogen of interest or the tumor associated antigen prior to step b).

* * * * *